(12) United States Patent
Dunlop (10) Patent No.: US 6,939,307 B1
(45) Date of Patent: Sep. 6, 2005

(54) METHOD AND APPARATUS FOR MONITORING HAEMODYNAMIC FUNCTION

(76) Inventor: Colin Dunlop, 132A Cressy Road, East Ryde, NSW 2113 (AU)

( * ) Notice: Subject to any disclaimer, the term of this patent is extended or adjusted under 35 U.S.C. 154(b) by 0 days.

(21) Appl. No.: 09/423,776

(22) PCT Filed: May 13, 1998

(86) PCT No.: PCT/AU98/00356

§ 371 (c)(1),
(2), (4) Date: Jan. 7, 2000

(87) PCT Pub. No.: WO98/51212

PCT Pub. Date: Nov. 19, 1998

(30) Foreign Application Priority Data

May 13, 1997 (AU) .............................. PO6763

(51) Int. Cl.$^7$ ................................................. A61B 5/00
(52) U.S. Cl. ...................................... 600/504; 600/526
(58) Field of Search ........................ 600/526, 500–505, 600/476–477, 481–483, 485, 301, 520; 514/816–818; 604/65–67, 27, 30, 28

(56) References Cited

U.S. PATENT DOCUMENTS

| | | |
|---|---|---|
| 4,414,980 A | 11/1983 | Mott |
| 4,548,211 A * | 10/1985 | Marks .................... 600/506 X |
| 4,695,576 A * | 9/1987 | Ekenstam et al. ...... 514/818 X |
| 4,739,772 A * | 4/1988 | Hokanson et al. .......... 600/544 |
| 4,784,150 A | 11/1988 | Voorhies et al. |
| 5,188,106 A * | 2/1993 | Nappholz et al. ....... 600/454 X |
| 5,490,506 A | 2/1996 | Takatani et al. |
| 6,016,444 A * | 1/2000 | John .......................... 600/544 |

FOREIGN PATENT DOCUMENTS

| | | |
|---|---|---|
| EP | 305080 | 3/1989 |
| EP | 378234 | 7/1990 |
| EP | 439018 | 7/1991 |
| EP | 771546 | 5/1997 |
| SU | 1364297 | 1/1988 |
| WO | WO 86/04225 | 7/1986 |
| WO | WO 87/00414 | 1/1987 |
| WO | WO 89/04634 | 6/1989 |
| WO | WO 92/08408 | 5/1992 |
| WO | WO 92/22248 | 12/1992 |
| WO | WO 94/02069 | 2/1994 |
| WO | WO 96/16594 | 6/1996 |
| WO | WO 96/32056 | 10/1996 |
| WO | WO 97/24980 | 7/1997 |

* cited by examiner

Primary Examiner—Robert L. Nasser
(74) Attorney, Agent, or Firm—Davis & Bujold, P.L.L.C.

(57) ABSTRACT

The present invention relates to a method and apparatus for monitoring haemodynamic function in animals and humans during anaesthesia and surgery. During anaesthesia and surgery the subject's haemodynamic, respiratory, neuromuscular and neurological functions are monitored as indicators of the condition of the health of the subject. Commonly, variations in blood pressure are used to imply corresponding variations in cardiac output, i.e. good blood pressure equals good cardiac output. The present invention utilizes a device to monitor changes of blood flow in peripheral blood vessels of the subject as an indicator of cardiac output. This is believed to provide a much more accurate indicator.

32 Claims, 6 Drawing Sheets

DISPLAY: DEFAULT SETTING

ANIMAL CLASS

| WEIGHT Kg | SPECIES | # |
|---|---|---|
| 1-5 | CAT/TOY DOG | 1 |
| 5-10 | SMALL DOG | 2 |
| 10-20 | MEDIUM DOG | 3 |
| 20-40 | LARGE DOG | 4 |
| 30 | SHEEP/GOAT | 5 |
| 150 | LLAMA/FOAL | 6 |
| 450 | HORSE | 7 |

AND SLOTS FOR "MEMORY"? 5

[RUN] [PAUSE] [DATA] [CLASS]

FIG. 4

DISPLAY: DATA ENTRY

| PULSE | RATE | DATA |
|---|---|---|
| | MIN | 000 |
| | BASE | 300 |
| | MAX | 300 |
| TONE | | |
| OFF | | |
| | TONE | ON |

| FLOW | RATE | DATA |
|---|---|---|
| | MIN | 0.0 |
| | BASE | 9.9 |
| | MAX | 9.9 |
| TONE | | |
| ON | | |
| | TONE | ON |

ANIMAL CLASS = NAME OR #

[RUN] [PAUSE] [DATA] [CLASS]

METHOD AND APPARATUS FOR MONITORING HAEMODYNAMIC FUNCTION

BACKGROUND OF THE INVENTION

The present invention relates to a method and apparatus for monitoring haemodynamic function in humans and animals and, particularly, but not exclusively, to a method and apparatus for monitoring haemodynamic function in humans and animals during anaesthesia and surgery, and its relationship to anaesthetic depth.

During anaesthesia and surgery on a human or animal subject, the subjects haemodynamic respiratory, neuromuscular and neurological functions are monitored as indicators of the condition of the health of the subject as anaesthesia and surgery progress. In general, as anaesthetic (depth) increases, haemodynamic, respiratory and neurological function are depressed or decrease (ie. there is a dose-dependent relationship). During any operation, it is important that adequate perfusion is maintained (ie. oxygenated blood reaches all vital organs including the brain, heart and kidneys). Tissue oxygen delivery is dependent on the level of perfusion or blood flow (cardiac output [CO]) and the amount of oxygen in the arterial blood (Arterial Oxygen Content, $CaO_2$). Haemodynamic function (causing blood flow to vital organs) is therefore carefully monitored and any changes which indicate that haemodynamic function may not be optimum will alert the anaesthetist who may adjust the anaesthetic does to compensate ie., to vary the depth of anaesthesia by adjusting anaesthetic depth.

Traditional monitoring of haemodynamic function in anaesthetised patients undergoing surgery, in particular humans, is based on cardiac auscultation, an ECG (electro cardiogram) and blood pressure measurement. Cardiac auscultation will detect the rate of heart beats. The ECG directly monitors cardiac rhythm (electrical rhythm of the heart) and indirectly monitors the pulse rate (assuming the electrical rhythm causes an organised heart muscle contraction). Blood pressure monitoring devices measure blood pressure, usually measure pulse rate and the information obtained is used by clinicians/anaesthetists to indirectly make inference about (estimate) haemodynamic function, i.e., cardiac output (total blood flow) and organ perfusion. The pulse rate, cardiac rhythm, blood pressure, and inference about haemodynamic functions provide the information necessary to give the anaesthetist an overall picture of haemodynamic function during anaesthesia and surgery.

This type of traditional monitoring of haemodynamic function, in particular the use of blood pressure monitors, is subject to a number of problems.

Indirect blood pressure monitors (systems using a pneumatic cuff and a method to detect the arterial pulse) are inaccurate in small animals, horses and human infants and automated devices can be expensive. Direct blood pressure monitors (systems using a catheter placed in an artery, connected to a pressure measuring device) are accurate but invasive, complex and expensive. Catheterisation of an artery is also NOT done without some risk of complication to the patient.

Further, the general perception in anaesthesia has been that good blood pressure equals good haemodynamic function. This is, if the blood pressure is good, it is taken as an indication that there is adequate blood flow to ensure perfusion of all the vital organs. During anaesthesia and surgery good blood pressure together with good results for the other indicators (cardiac rhythm, pulse rate, etc) has generally been taken to mean that everything is going well for the patient.

The majority of anaesthetic agents depress cardiac output in a dose dependent fashion. Generally, therefore, low blood pressure has been taken to indicate that anaesthetic dose should be lightened and high blood pressure that anaesthetic does should be increased (although the other indicators also have a bearing on anaesthetic does and the anaesthetist will take all indicators into account before deciding on the appropriate action).

The present applicants have realised that blood pressure is not in fact as good an estimator of cardiac output or perfusion during anaesthesia and surgery as has traditionally been considered. Firstly, indirect measurement of blood pressure is inaccurate and secondly it is, in fact, frequently negatively related to total blood flow (cardiac output) and tissue oxygen delivery.

There is a recognised relationship between blood pressure, cardiac output and vascular resistance, as follows:

Cardiac Output =Blood Pressure (Map–Right Artrial Press)+Vascular Resistance.

One major problem with the usual assumption that blood pressure gives an indication of cardiac output is that none of the usual clinical measurements (auscultation, electrocardiogram, blood pressure) provide any information about vascular resistance.

During surgical procedures at usual anaesthetic levels, it is believed that the subject body may still experience and respond to painful stimulation, although the subject is not consciously aware of the pain. The body, however, produces its standard sympathetic nervous system response to the painful stimuli, including catecholamine release, resulting in vasoconstriction. The applicants believe that such responses lead to increases in blood pressure during surgery being accompanied by a decrease in cardiac output. This is exactly opposite to the relationship between blood pressure and cardiac output which clinical anaesthetists have traditionally assumed. During painful surgery, therefore, rather than a direct positive relationship between blood pressure and blood flow there is believed to be a variable relationship which may even be in a negative direction.

Given the above observation, and also the fact that non-invasive blood pressure monitors are inherently inaccurate, it is clear that, in anaesthetised patients undergoing surgery, blood pressure cannot be relied on as an accurate estimator of haemodynamic function.

SUMMARY OF THE INVENTION

The present invention provides a method of monitoring haemodynamic function in a human or animal subject, comprising monitoring changes in blood flow in a peripheral blood vessel or tissue bed, to provide an indication of changes in cardiac output.

The method preferably finds most application during anaesthesia and surgery.

It is believed by the applicant that the monitoring of changes in peripheral blood flow will provide a more accurate indication of changes in cardiac output than that inferred from monitoring blood pressure. It is thought that an increase in blood flow in a part of the body is more likely to indicate an increase in cardiac output, as compared to an increase in blood pressure, considering the limitations discussed above relating to using blood pressure as a cardiac output indicator during anaesthesia in surgery.

In anesthesia and surgery, it is all important that haemodynamic function be maintained such that sufficient oxygenated blood reaches the vital organs, e.g. brain, liver, etc. Good cardiac output is a good indicator of whether there is sufficient blood flow to perfuse the vital organs, particularly during anaesthesia where patients usually breathe high inspired concentrations of oxygen.

Blood flow in an anaesthetised subject may be monitored in a number of ways. Cardiac output can be monitored directly, using indicator dilution techniques such as by the insertion of a pulmonary artery, thermo-dilution, cardiac catheter, for example. This method is intermittent, invasive, requiring cardiac catheterisation, which is not risk free and is not preferred, although insertion of such catheters provides an accurate measurement of total blood flow (cardiac output). Indirect cardiac output or aortic blood flow measurement may also be made using 2 or 3-dimensional pulsed Doppler cardiac ultrasound, but with computer generated colour flow enhancement display this is very expensive, not accurate, technically difficult and is very sensitive to probe position, movement of the subject or the measuring probe such as occurs during surgical manipulation. In addition it requires a person to continuously hold the transducer on the body in a constant position.

There are a number of devices on the market which the applicant has found could be adapted for monitoring blood flow in blood vessels or tissue beds, non-invasively, relatively inexpensively and generally being relatively non-movement sensitive. Such devices are particularly suitable for monitoring changes in blood flow in peripheral blood vessels, which the applicants believe will still provide a relatively good indication of changes in cardiac output. The method of the present invention is preferably applied by continuously monitoring changes in blood flow, preferably in a peripheral blood vessel, to provide an indication of, changes in cardiac output. For practical clinical application, it is preferred to monitor blood flow in parts of the body where access is easier and, in particular, blood flow in peripheral blood vessels. It may be difficult to measure the actual blood flow in a peripheral blood vessel as, unless an invasive technique is used, the diameter of the peripheral vessel(s) can only be estimated. Changes in blood flow in peripheral vessel(s) can be monitored reliably, however. These changes can be used to estimate changes in cardiac output (total blood flow) we believe, quite reliably. Changes in blood flow in the peripheral vessel during anaesthesia and surgery can, therefore, be utilised by the anaesthetist to adjust dose, eg. if blood flow in the peripheral vessel should fall, then the anaesthetist can imply corresponding falling cardiac output and can reduce anaesthetic dose to compensate (also taking into account other monitored factors, as discussed above). Changes in blood flow in the peripheral vessel, therefore, give a relative indication of changes in total blood flow (cardiac output).

Blood flow devices are known which detect blood flow in peripheral blood vessels of subjects, by employing an ultrasound sensor which uses the Doppler effect to detect either red blood cell motion or blood vessel wall motion. A signal is produced to simply indicate that motion is occurring (ie. the signal is either on or off/present or absent). An example of such a device is produced by Parks Electronics of Aloha, Oreg., USA. Presently, such a peripheral blood flow monitor is used together with a occlusive cuff and aneroid manometer to indirectly measure blood pressure. The occlusive cuff is tightened to the point that the monitor registers that there is no blood flow in a peripheral artery and the pressure is then read from the manometer. This method only allows the operator to obtain systolic arterial blood pressure. The Doppler monitor is therefore only used in this application to determine whether there is blood flow or whether there is not any blood flow, ie. "on" or "off".

A more advanced continuous wave Doppler device can print a pulsatile wave form based on the frequency and volume of the reflected Doppler, and calculate the peak and mean velocity of the blood flow. Such a device is manufactured by Hiashi Denki Company Limited in Japan (the ES-1000 SPM and E9-1000 SP).

As far as the applicants are aware, no such Doppler monitor has been used for the purpose of monitoring haemodynamic function during anaesthesia. Indeed, none of the prior art devices are suitably adapted to be useful for use in such an application.

The present applicants have utilised a Doppler ultrasound device as a blood flow monitor, to provide a signal whose characteristics preferably varies depending on the amount of blood flowing in a particular peripheral artery, in order to provide at least a relative indication of changes in total blood flow (cardiac output). This device is used in one preferred embodiment of the method of the present invention.

Pulse oximeters measure the absorption of infra-red radiation by red blood cells in a peripheral vascular bed in order to determine the oxygen saturation of the blood. Since the amount of infra-red radiation absorption depends on the amount of blood, such a device may be adapted, in accordance with an embodiment of the present invention, to provide an indication of relative changes in blood flow in the peripheral vascular bed. This measurement of changes in blood flow may be used as an indication of changes in total blood flow.

In yet a further embodiment, a colour chart may be utilised to estimate changes in blood flow in a tissue bed that has a high density of superficial blood vessels by reference to the colour of the mucous membrane in that tissue bed, eg. gums, tongue, lips, etc. Again, this provides a relative estimate of changes in total blood flow. Colour charts are designed by clinical observation of control subjects under various conditions and relating the observed colour to measurements of blood flow. In the limit, a colour chart is not even necessary to carry out the method of the invention, mere practiced observation of an appropriate tissue bed by a skilled anaesthetist could be used to estimate changes in mucous membrane colour and therefore in blood flow in that area and therefore provide a relative estimate of total blood flow.

The information obtained from monitoring blood flow will be used together with information from an electro cardiogram and measurement of blood pressure to provide a total picture of the haemodynamic condition of a subject during anaesthesia and surgery. This will give sufficient information for the anaesthetist to properly evaluate the haemodynamic condition of the subject and vary anaesthetic dose accordingly.

Preferably, where a blood flow monitor is used, the method of the present invention includes the further step of applying a regression analysis to the signal produced by the blood flow monitor. Preferably, the regression analysis applied involves the steps of monitoring in an animal or human subject either cardiac output, tissue $0_2$ delivery (in a subject under anaesthesia breathing a high inspired amount of $0_2$, arterial oxygen content is generally constant as changes in tissue oxygen delivery reflect changes in cardiac output) against the signal from the blood flow monitor. The data can be used to produce a plot which can be described by regression analysis. The regression equation can be used to calibrate the actual output of the blood flow monitor to provide a more accurate relative indication of CO or tissue oxygen delivery.

Preferably, the method also includes the further step of making a further adjustment to the signal output by the blood flow monitor by applying changes in heart rate as a co-variant factor. This has been found to further improve the estimate of CO of tissue oxygen delivery.

The present invention further provides a device for monitoring haemodynamic function in a human or animal subject, comprising a blood flow monitor arranged to monitor changes in blood flow in a peripheral vessel or tissue bed, to provide an indication of changes in cardiac output.

Changes in blood flow in a peripheral vessel can preferably be used to provide an indication of changes in cardiac output. By "changes in blood flow" is meant changes of degree, not merely presence or absence of flow.

Preferred blood flow monitors are able to non-invasively monitor blood flow in peripheral blood vessels and provide an output signal who's characteristics vary depending upon actual blood flow in the peripheral vessel(s) being monitored. As discussed above in relation to the previous aspect of the present invention, changes in blood flow in a peripheral vessel provides a relative indication of changes in total blood flow (cardiac output). Preferably, the device comprises a display or indication means, and means for receiving the signal from the blood flow monitor and processing it to drive a display or other indication means to provide an indication of blood flow, preferably changes in blood flow, which can be monitored by the clinician, such as an anaesthetist.

In a preferred embodiment, the device may be pre-calibrated for a particular subject by, firstly, taking the strength of the blood flow signal from the blood flow monitor when the patient is at rest prior to induction of anaesthesia and surgery and, then using an occlusive cuff to shut off blood flow to the peripheral vessel, obtaining a zero signal. The display on the device can then preferably be set between the upper rest resting blood flow rate and the zero blood flow rate. The device preferably includes an alarm warning indication means to provide an indication of an alarm situation, if the blood flow in the peripheral vessel drops below a certain pre-determined amount.

The device is preferably adapted to give an output which is particularly designed to be useful for an anaesthetist monitoring a subject under surgery. The display preferably provides indications of changes in blood flow in the patient and, preferably, an alarm is provided to sound or provide an indication of an alarm condition when a blood flow change occurs which indicates that a person is either anaesthetised too deeply or not deeply enough. The display may be graded with markings indicating the changes in blood flow in relation to anaesthetic conditions, i.e., too much anaesthetic, too little anesthetic, etc.

The device is also preferably arranged to apply an adjustment factor to the blood flow monitor signal, the adjustment factor being based on a regression analysis of actual subjects. The device is also preferably arranged to provide a further adjustment to the signal by taking a co-variant as an input to adjust the signal, and preferably, the co-variant is heart rate. The adjustment preferably results in an improved output signal.

The blood flow signal may be derived from a pulse oximeter, Doppler monitor, as discussed above.

In an alternative embodiment, the blood flow monitor may comprise a colour chart including coloured patches to be compared with an area of the body of the subject, eg. the lips or tongue. The colour chart would be pre-determined for an "average" subject of the particular animal type (or human being) to give an indication of blood flow depending upon the colour of the body part at the time.

A blood flow monitor and method in accordance with the present invention may have applications other than during anaesthesia. For example, a device which is arranged to monitor changes in blood flow in peripheral vessels or peripheral tissue beds may have application in cardiac stress testing, and other applications.

BRIEF DESCRIPTION OF THE DRAWINGS

Features and advantages of the present invention will become apparent from the following description of embodiments thereof, by way of example only, with reference to the accompanying drawings, in which.

DESCRIPTION OF THE PREFERRED EMBODIMENTS

A device in accordance with an embodiment of the present invention, for use with a method in accordance with the present invention, is illustrated in FIGS. 1 through 7. The device can be used as discussed in the preamble, to monitor changes in blood flow in a peripheral blood vessel of a human or animal subject during anaesthesia and surgery. This gives an indication of relative changes in total blood flow (cardiac output) as one of the indicators for enabling the anaesthetist to monitor the subjects haemodynamic condition and suitably adjust anaesthetic dose. Monitoring peripheral blood flow to provide an indication of changes in cardiac output, as opposed to using blood pressure, runs contrary to anaesthesia practice over the past one hundred years where blood pressure is used in surgery to indicate changes in haemodynamic function or cardiac output. As discussed above, the present applicants believe that, because of responses to painful stimuli during surgery, blood pressure is neither a reliable or positive indicator of changes in cardiac output. They believe that either monitoring of total blood flow or, as in the preferred embodiment of the invention, monitoring of changes in blood flow in a peripheral artery during anaesthesia in surgery, will provide a much better positive indication of relative changes in total cardiac output.

The method of monitoring haemodynamic function during anaesthesia and surgery in accordance with the preferred embodiment of the present invention, also preferably includes the steps of monitoring blood pressure, using standard equipment, monitoring ECG, using standard equipment and monitoring respiration using an airway thermistor. The heart rate may be monitored using the ECG device. The pulse rate may be monitored using the device in accordance with the present invention, being determined from the peripheral blood flow. These parameters, together with blood flow, provide the total "picture" required by the anaesthetist to enable monitoring and adjustment of anaesthetic dose to ensure the haemodynamic health of the subject.

Figure 1:
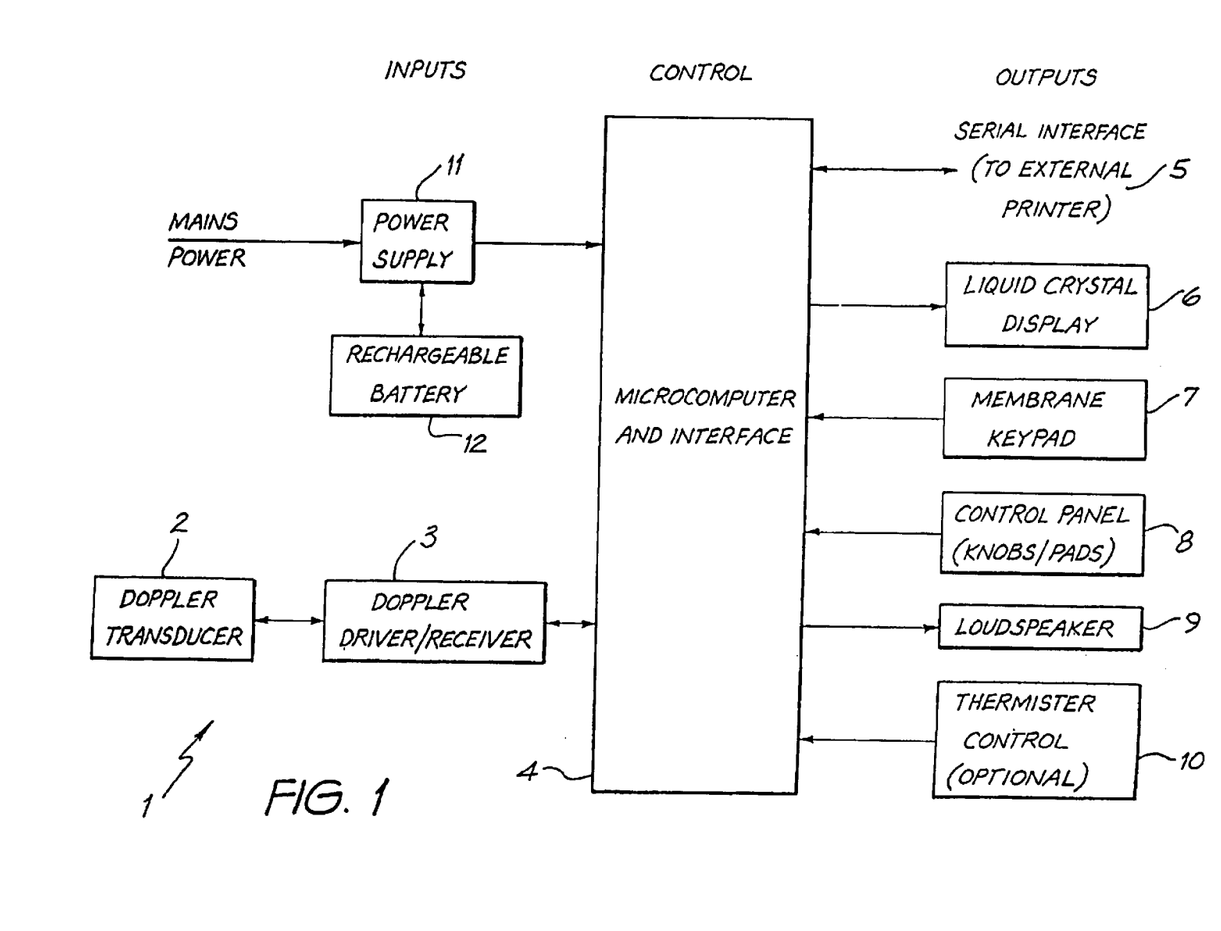
FIG. 1 is a schematic block diagram of a device in accordance with one embodiment of the present invention.

FIG. 1 is a functional block diagram showing components of an ultrasound based device for monitoring blood flow, in accordance with an embodiment of the present invention. The device, generally indicated by reference numeral 1, comprises a Doppler transducer 2 for monitoring blood flow in a peripheral blood vessel of a human or animal subject. In operation, the transducer will be affixed to the appropriate body part of the subject eg. placed distally on the wrist or ankle of a human being, or where an animal is the subject, on the tail. Note that as an alternative to a Doppler transducer 2, a pulse oximeter adapted to monitor blood flow could be used as the blood flow detector (transducer). In fact, any device which is capable of detecting blood flow, in the preferred embodiment in a peripheral vessel, could be used.

Note that a further alternative, in accordance with an alternative embodiment of the present invention, is to use a device such as a pulse oximeter in addition to using the Doppler transducer 2 to monitor the changes in blood flow. The pulse oximeter is, in accordance with this embodiment, adapted to monitor blood volume in a peripheral tissue bed (rather than oxygen saturation which is usually constant during anaesthesia where patients inspire high concentrations of oxygen) and this may be used to improve the estimate of changes in blood flow or to enable estimation of changes in vascular resistance. In this alternative embodiment, the device of FIG. 1 would also include a sensor and a pulse oximeter device providing an input about changes in tissue blood volume to the micro computer 4 for processing together with the perfusion input from the Doppler device. The following description, however, relates to an embodiment which employs a Doppler monitor only.

In this embodiment, a continuous wave Doppler driver/receiver 3 is connected to the Doppler transducer for transmitting and receiving ultrasound signals therefrom. A microcomputer and interface 4 is arranged to process the signal from the receiver 3, and drive the LCD display 6 to produce an output indicative of changes in cardiac output (substantially equivalent to tissue oxygen delivery under high inspired concentrations of $0_2$). It also controls and/or responds to the other peripherals, as follows:

a serial interface 5 to an external printer;

a liquid crystal visual display 6;

a membrane keypad 7;

a control panel 8;

a loud speaker 9; and a thermistor controller 10 for controlling a airway thermistor (not shown).

Power is provided from the mains via a power supply regulator 11, which is also provided with a back-up rechargeable battery 12, in case of failure of the mains.

In operation, the microcomputer of controller 4 operates to process the signal from the Doppler transducer 2 to determine changes in the blood flow rate in the peripheral vessel and to control the liquid crystal display 6 to provide an indication, preferably graphical indication, of the instantaneous relative cardiac output at any time during anaesthesia and surgery. It is preferred to give an output of relative cardiac output, rather than attempting to produce an output indicative of actual cardiac output. Attempting to obtain a measurement giving actual cardiac output is very difficult because a) vessel diameter is required or b) it assumes that changes in blood flow or vessel diameter in one vessel similarly reflect changes in the whole animal. Monitoring changes in blood flow to provide an output relative to a reference, such as the signal output by the blood flow monitor when the patient is at rest prior to anaesthesia and surgery, is much more convenient, and provides sufficient indication to the anaesthetist to guide him to control anaesthetic depth. The loudspeaker 9 is controlled by the controller 4 to provide an audible pulse signal and alarms should the blood flow fall below or rise above pre-set levels. Preferably, the display 6 also provides a visual alarm indication. The control panel 8 can be used to pre-set the blood flow display and alarm limits, depending upon, for example, the size of the subject and the species of the subject. It is envisaged that a device would be provided suitable for operation on a human subject and a separate device suitable for operation on animal subjects, the animal subject device preferably being adapted for use with a number of animal species, control limits being pre-set for species and animal size by the control panel 8. The microcomputer and interface 4 is arranged to process the Doppler signal output to give an indication of blood flow changes based on the strength of the signal.

Figure 2:
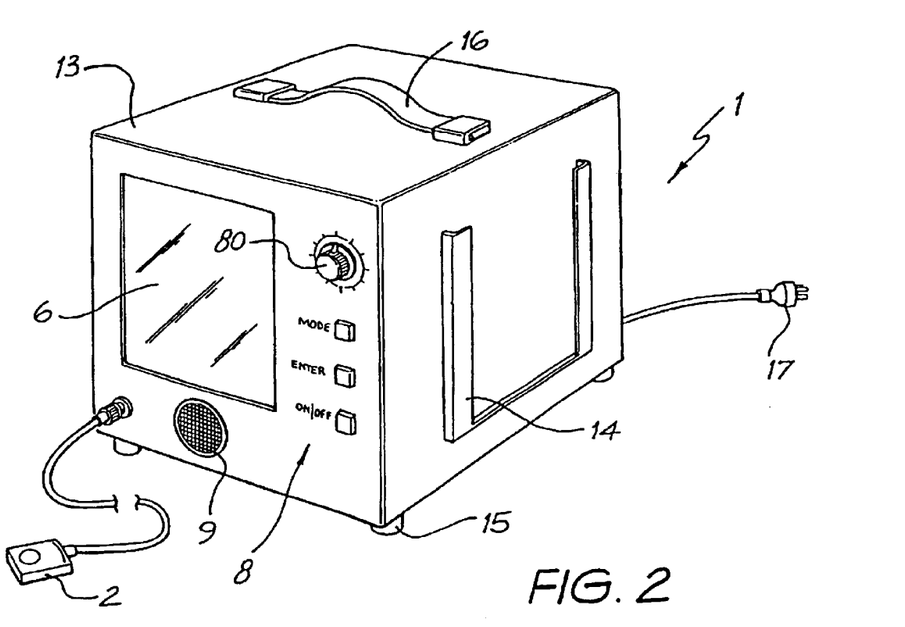
FIG. 2 is a schematic perspective view of a external appearance of a device in accordance with the embodiment of FIG. 1.

FIG. 2 shows the external appearance of an example device 1. Equivalent items to FIG. 1 are given the same reference numerals. The entire device 1 is housed within a robust housing 13. Brackets 14 are provided to hold a reference manual giving operating instructions on the device 1. The device is mounted on rubber feet 15 and has a carrying handle 16. A plug 17 is provided for connection to a mains power supply.

In operation, before a subject is anaesthetised, the Doppler transducer (sensor) 2 is positioned on the skin surface, overlying a peripheral artery such as located in the human forearm at the level of the wrist (radial or ulna artery), on the plantar surface of the foot of a dog or cat (pedal artery) or on the ventral surface of the tail (coccygeal artery). The device is attached to the subject at rest while conscious and a flow rate determined. The control pad 8 is then used to set a "base line flow" rate and a base bar (reference number 20, FIG. 3) will appear on the operating display. The base bar will be used as a reference by the anaesthetist as the "normal" flow rate of the conscious resting subject (ie. prior to induction of anaesthesia). As an alternative, the device may also be arranged to store a series of "standard" base bars, being default settings for a particular animal species/size of animal. This would be necessary for animals which may not tolerate attachment of the transducer while conscious. For a human subject, however, it is preferable to pre-set the levels and the display by monitoring of the individual subject.

Figure 3:
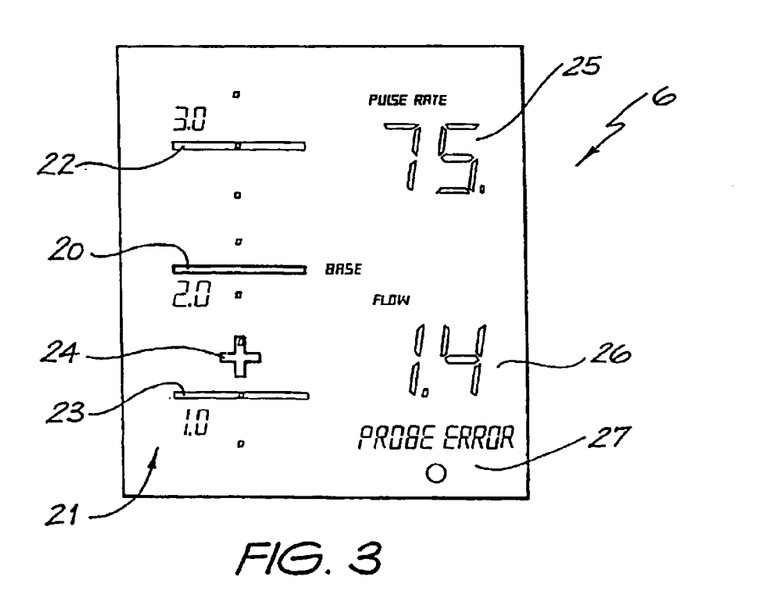
FIG. 3 is a view of an example operating display of the device of FIG. 1, for a human subject during anaesthesia in surgery.

FIG. 3 shows an example operating display for a human subject during anaesthesia and surgery. The left hand side of the display, indicated by reference numeral 21, is taken up by a bar graph which graphically continuously indicates peripheral blood flow rate based on the signal obtained from the peripheral vessel, processed by the controller 4 to provide the display. The base bar 20 is permanently in place on the graphical display and is pre-set by monitoring the flow rate of the conscious subject at rest, prior to the induction of anaesthesia. All flow rates and flow alarms are determined relative to this base bar 20. A high limit bar 22 and low limit bar 23 are also displayed. These can either be pre-set by the anaesthetist or pre-stored in memory to automatically be displayed depending upon the set base bar level and other subject factors, eg. weight, age, etc. For example, appropriate limits could be determined by clinical trials and then stored in the memory of the device.

A moving flow marker 24 is also displayed. This shows the actual real-time flow rate (relative to the base bar). It is this marker 24 that the anaesthetist will watch carefully to obtain an indication of changes in haemodynamic function. Preferably, the flow marker is arranged to flash. Should the rate fall to the lower limit bar 23 or rise to the high limit bar 22 an audible alarm will sound and the numeric flow display 26 will flash. The anaesthetists attention will thus be drawn to the alarming level of perfusion or blood flow and appropriate action can be taken (eg. altering anaesthetic dose, administration of IV fluid, inotropic drugs etc.). Note that it is unlikely during appropriate levels of anaesthesia during surgery in normal, healthy patients that blood flow will ever rise much above the base bar. This is because standard anaesthetics tend to depress (rather than stimulate) cardiac output in a dose dependent fashion. Such a monitoring device can also be used for monitoring haemodynamic function during critical care such as post cardiac surgery. On this point, a novel device such as this is likely to provide precise clinical data on the effect of anaesthetics and surgical manipulation on peripheral blood flow in humans and animals. However, there are applications of this device, such as cardiac stress testing (treadmill testing) or conscious humans or race horses, where blood flow could increase above the base line measurement.

Referring again to FIG. 3, the controller 4 also determines the pulse rate of the subject from the Doppler flow signal. This is displayed in the top right hand portion 25 of the display 6. The anaesthetist can also therefore view pulse rate, at a glance. The bottom right hand corner of the display 26 displays the actual (instantaneous) peripheral blood flow rate in alphanumeric.

Should the probe signal change caused by transducer or skin movement relative to the artery or loss of acoustic coupling or otherwise malfunction, a "probe error" display will flash 27.

Switching the device on and taking no further action defaults the screen to the monitoring display (FIG. 2). All input and control of the device is set by rotating knob 80 (FIG. 2) to select function or value and pressing enter to accept function or value.

Upper and lower limit thresholds may also be set for pulse rate, such that if the thresholds are reached audible alarms/visual alarms are provided. A breath to breath audible output and a numeric display of respiratory rate, may also be provided if an airway thermistor is employed.

Figure 4:
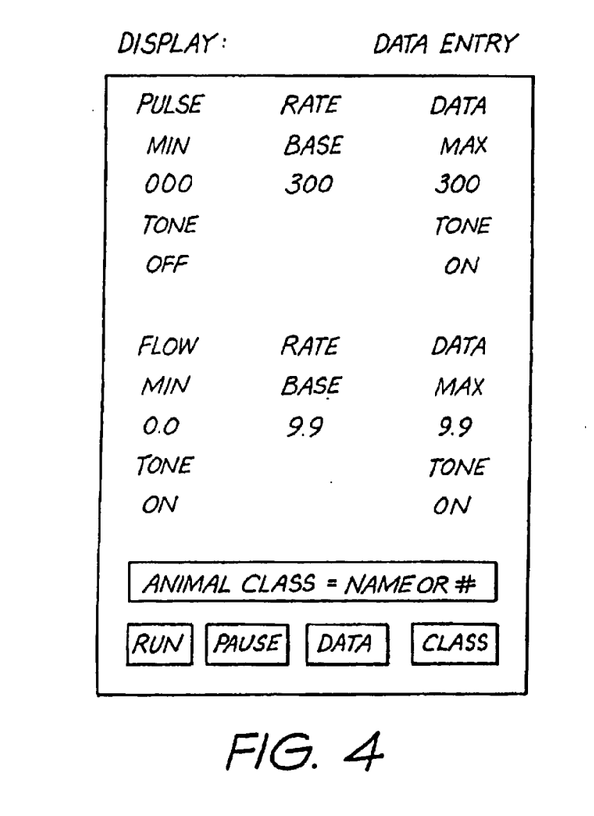
FIGS. 4 and 7 show various displays of the programming (set up) and alarm setting functions, displayed as for animal operation.

FIGS. 4 through 7 show examples of screen displays which may appear during initial set up of the apparatus prior to operation on a human or animal subject. The example screens are based on the device as designed for animal use. This is generally the same as what would appear in the device as designed for human subjects, except that it is envisaged that there would be no screen for default species settings (FIG. 5) although default settings based on body size could be introduced. Alternatively, all the settings for the alarm function could be entered manually (FIG. 4). After selecting either the default settings (FIG. 5) or entering the alarm settings manually (FIG. 4), the device will then display the result and settings as selected (FIG. 6) before reverting to the "running" display associated with the continuous monitoring function (a running display is shown in FIG. 3 for a human being, but a similar display would be shown for animal).

The boxed items of display (FIG. 4) ("Run", "Pause" etc) are what can be selected by turning the knob 80. A selected function displays as inverse display (ie. white letters on black background). Depressing the knob will then cause the numerical value to increase in magnitude to a maximum number. Subsequently turning the knob by 10° will move the selection to the next boxed item in a left to right, top to bottom flow with wrap-around at bottom. Turning the knob counter clockwise will reverse the selection highlighting.

FIG. 4 shows a typical data entry display for manual entry of the alarm settings, which enables entry of pulse rate high/low limits and flow rate high/low limits ie. minimum, base and maximum levels for each item. These values can be set manually based on the preference/clinical experience of the anaesthetist. Alternatively, selection of alarm limits may be based on default settings as shown for animals.

Figure 5:
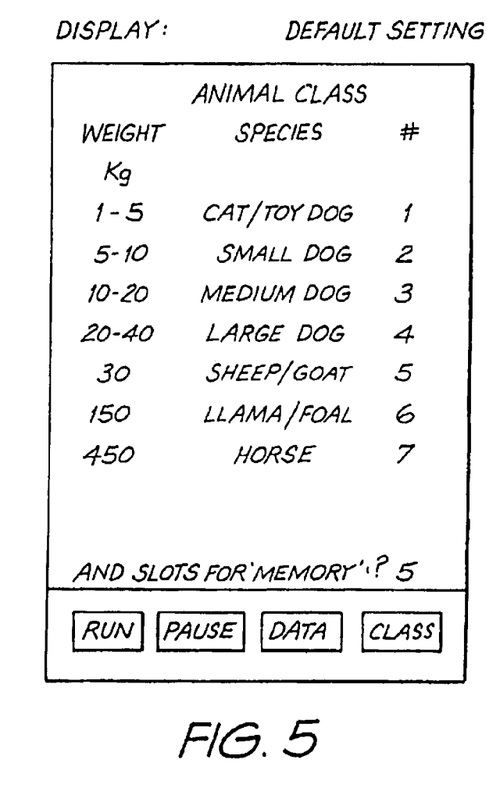
Figure 6:
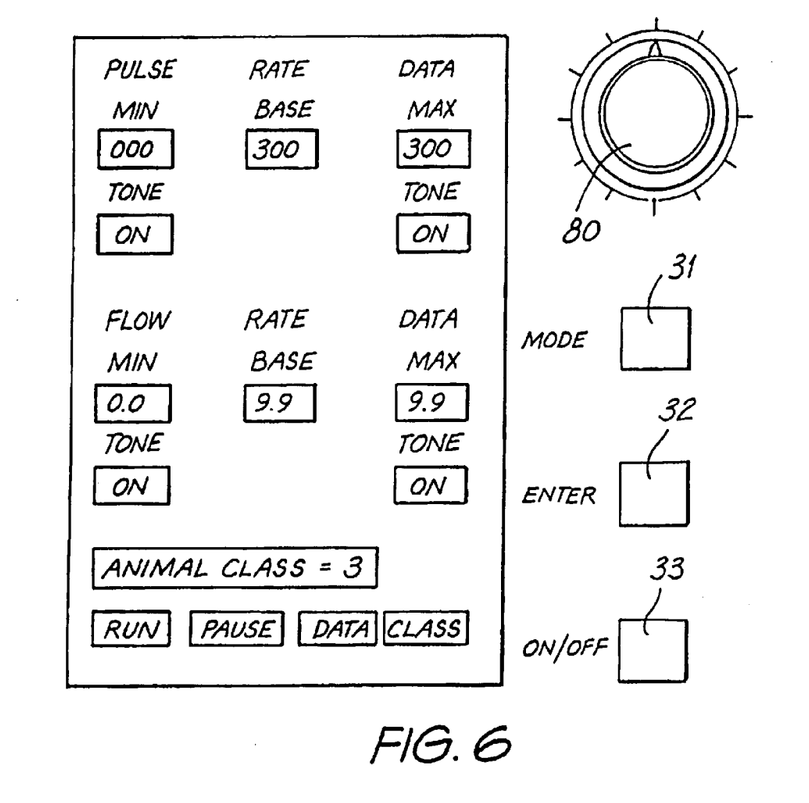
Figure 7:
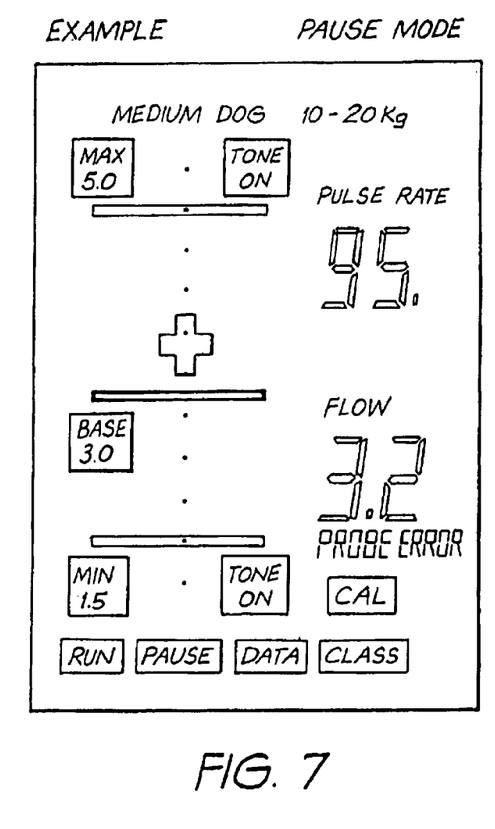

FIG. 5 shows a display for default settings which can be selected, which will be based on clinical trials for the particular species/weight of animal (Note that manually five entered default settings may be stored by the user in memory). FIG. 6 illustrates the screen with the default settings which were either entered manually (FIG. 4) or selected (FIG. 5). Devices may obviously be designed with different default settings for different species and animal sizes, depending upon application.

FIG. 6 is a diagram of the entered/selected alarm setting display, also showing the rest of the control panel from FIG. 2, incorporating screen selection knob 80, mode button 31, enter button 32 and on/off switch 33.

For this example (10–20 kg dog) using FIG. 6 "enter" can be pressed while the selection knob is set on "Animal Class" to display the Animal Class display from FIG. 5. A 10–20 kg dog will be class "3", the knob is turned 10° clockwise to highlight the numerical animal class function number 3 which results in the various high/low default limits shown in FIG. 6. Enter button is then pressed which now selects the default settings (for class number 3) and changes the display screen to FIG. 6. Turning the knob 5° will increment by one value resulting in the display value being 1. Thus turning the knob to approximately 55° clockwise will set the value to 11 (a 15 kg dog). The knob can be rotated counter-clockwise to decrement the values. Again the "enter" button is pressed which records and accepts the value. At this point all the values on the Data Enter display will change to the default values for a 15 kg dog. The highlighted box will move to the RUN box assuming the "enter" button will be pressed to accept all the default values and change the display to FIG. 7—If a Run Display of particular value is to be changed, eg. warning tone to OFF, the knob is turned either clockwise or counter-clockwise to the desired box. Pressing enter will toggle the value (to on/off etc) and move the selection to next value (left to right, top to bottom). When all values on the Data Enter display are set and RUN is entered, the display changes to the RUN display.

In the PAUSE mode (FIG. 7), the display will be inverse. All Data Enter values will be display on the RUN display format.

The Doppler sensor is secured with the animal sedated.

RUN is selected by turning the knob counter-clockwise approximately 10° and "enter" button pressed. The monitor will now start to function, updating the display approximately every 15 seconds, showing heart rate, flow, and moving the flow marker above or below the base value. At any time during operation the knob can be turned to highlight any value on the run display.

During the procedure, the base value may need to be adjusted. Such as with re-positioning the patient for surgery. Turn the knob to highlight the base value eg 2.0 FIG. 3, press enter, turn the knob (clockwise or counter-clockwise) to display the desired base flow, then press enter. The monitor will accept the new base flow number and readjust the High/Low limit bars.

With regard to the embodiments discussed above, the output signal from the Doppler transducer is a signal the amplitude and/or frequency of which varies depending upon the rate of blood flow in the peripheral vessel being monitored. As discussed above, the signal can therefore be processed by the micro computer 4 to control a display to give an output indicative of changes in total blood flow as the changes in blood flow in the peripheral vessel correlate with changes in total cardiac output (CO). In a clinical situation, such as during anaesthesia in surgery, the accuracy of this correlation is important, i.e., it is important that the displayed changes correlate well with the actual changes in cardiac output or tissue oxygen delivery. If the display gives an inaccurate reading, particularly in the critical range (i.e., in the region of the alarm levels) then information given to the anaesthetist can be misleading and ultimately lead to a dangerous situation.

The present applicants have found that the accuracy of the correlation between the changes in the output signal from the Doppler transducer and changes in cardiac output can be much improved by further processing of the signal to adjust the signal by a factor which is based on regression analysis of actual experimental subjects. They have also found that the correlation can be even further improved by adjusting the processed signal by employing a co-variant factor, in the preferred embodiment being heart rate. Adjustment of the signal using these factors preferably leads to a more accurate output and the microprocessor is preferably arranged to process the signal from the Doppler transducer by including adjustments based on these factors.

Figure 9:
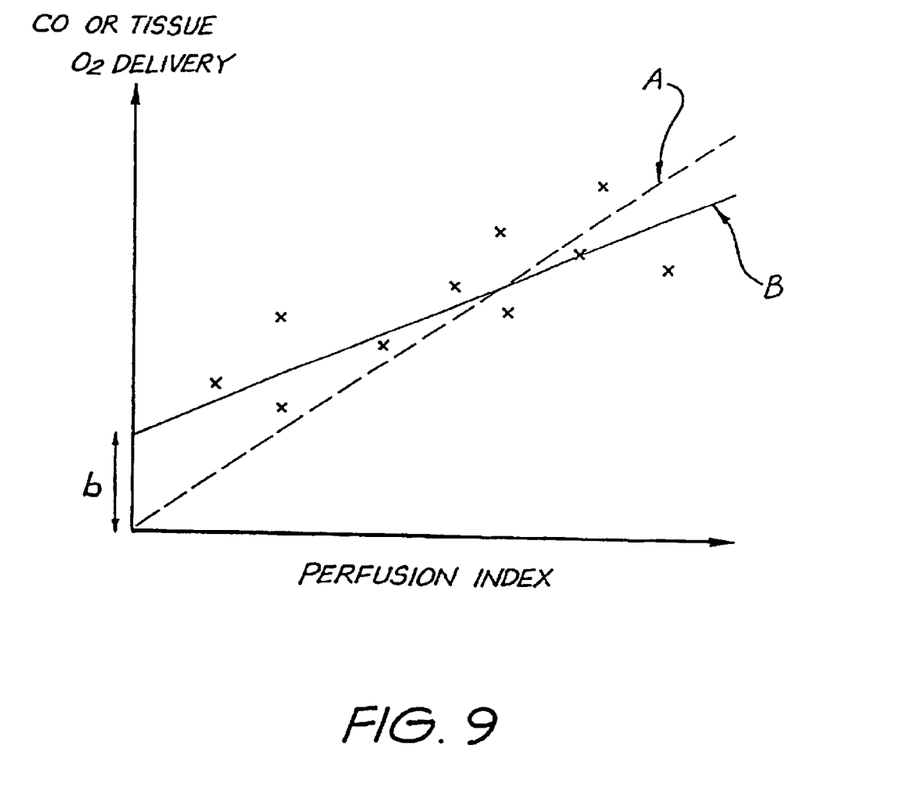
FIG. 9 is an example plot of cardiac output or tissue $0_2$ delivery against "perfusion index" to demonstrate how regression analysis is to be applied to the output signal of a blood flow monitor in accordance with an embodiment of the present invention.

FIG. 9 is a schematic plot of "Perfusion Index" in relation to cardiac output (CO) or tissue oxygen delivery, for a notional experimental subject, to illustrate how regression analysis may be applied in accordance with this embodiment of the invention. Perfusion Index is a term the applicants have chosen to represent the processed output of the Doppler device (or where another device is being used to monitor blood flow, the output from that device). The processed signal from the Doppler device, which is a voltage output proportional to doppler frequency change, whether it be amplitude or frequency, provides an output known as the Perfusion Index. Ideally, this output will be directly proportional to cardiac output or tissue oxygen delivery (curve A of FIG. 9). During anaesthesia, high inspired amounts of oxygen are applied so that the arterial oxygen content is relatively constant. Changes in cardiac output can be taken to be substantially the same as changes in tissue oxygen deliver, therefore, in these circumstances.

The ideal, unfortunately, is not the case. From experiments with subjects, however, it is possible to plot Perfusion Index against CO or tissue oxygen delivery, by monitoring cardiac output with another device arranged to directly monitor cardiac output, and by applying a device such as a Doppler monitor to monitor "Perfusion Index", on an experimental subject, to give a realistic plot, plot A in FIG. 9. The equation for the curve is:

$$y=a+b$$

where y is in this case cardiac output or tissue oxygen delivery, x is Perfusion Index, a is the slope and b is the intercept (see FIG. 9).

By adjusting the output of the Doppler device by modifying it by a factor corresponding to a and b, i.e., modifying it by using a regression analysis employing a experimental subject, a more accurate correlation of Perfusion Index (i.e., the new adjusted Perfusion Index) with cardiac output or tissue oxygen deliver can be obtained. In the preferred embodiment, therefore, the micro computer 4 is arranged to modify the output of the Doppler receiver 3 by a factor relating to the regression analysis. This has been found to provide a much improved output, i.e., a more accurate indication of the cardiac output.

In application, therefore, regression analysis is carried out by a monitoring perfusion index against cardiac output or tissue oxygen delivery for a plurality of subjects. The results of the regression analysis are then used to calculate a weighting factor to be applied to the output from the Doppler monitor, by the device in accordance with the embodiment of the present invention, in order to adjust that output to create a more accurate output indicative of cardiac output or tissue oxygen delivery. In the example given in FIG. 9, a and b are calculated and y with the new adjusted output, is produced in accordance with the formula y=ax+b.

Note that tissue oxygen delivery=tissue blood flow (cardiac output) x arterial oxygen content.

A further improvement to the correlation of Perfusion Index to cardiac output can be made by further modifying the output signal from the Doppler transducer by making an adjustment for a co-variate factor.

Cardiac output=heart rate×stroke volume.

Cardiac output also=mean arterial pressure/vascular resistance.

There are therefore a number of variants which influence cardiac output and which may also determine the accuracy of an output signal from the Doppler monitor. The applicants have found that, in patients anasethetised for surgery, including a co-variate factor based on heart rate also results in an increase in the accuracy of the final output of the device. A co-variate factor relating to mean arterial pressure does not improve the output and in fact degrades it.

Preferably, therefore, in accordance with the preferred embodiment of the invention, the output of the Doppler monitor is also adjusted by applying a co-variate factor, based on the heart rate of the patient. Again, a number of experimental subjects are monitored to see what variation of the output of the Doppler monitor (perfusion index) occurs with pulse rate. A weighting factor is then applied to the output from the signal in accordance with detected heart rate for a patient, to further improve the response of the device.

A further modification which may be made to the device is to process the output to provide an indication of the "trend" of the output and also provide a display of the trend. All measurements are stored periodically, for example every one to five seconds, and a display which gives the direction that the output is taking, i.e., either up or down, is provided for the anaesthetist. This "trend" display can be useful in anaesthesia, and will generally provide more direction to an anaesthetic as far as anaesthetic dose required is concerned, than a straight forward "number" display not indicating any trend.

As discussed above, the preferred Doppler device to be used with the present invention is a continuous wave Doppler. These are preferably cheap, easy to build and portable. In operation, the ultra sound beam is transmitted from one crystal and the reflected wave received by another. The change in frequency of the reflected signal is in part due to the velocity of the red blood cell flow. The change in the amplitude of the signal depends on the vessel, distance and tissue density differences.

Vessel wall motion alters the high amplitude, of the signals which influences the shape of the amplitude/time spectrum of the reflected wave. This problem can be minimised by using Doppler crystals with higher sound frequencies (8 to 10 MHz). In addition use of front end clutter filters designed to optimise the illumination of reflected sound from skin, subcutaneous tissue and fat can be employed, and this is preferred. Since the amplitude and time lay of the reflected noise depends on the depth and size of the blood vessel being analysed, the filters are preferably specific for either body size (e.g., adult human, child or neonate) or species (e.g., cat, dog, horse). A toggle switch preferably enables the operator to select the desired clutter filter (not shown in the figures).

The change in time difference between the reflected signal from the proximal and distal wall of the blood vessel can be analysed and will indicate changes in blood vessel diameter. An estimate of blood vessel diameter combined with the estimate of velocity of blood flow, can be used to give index of blood flow, which can be modified in accordance with the factors discussed above to give the desired output (perfused index) which accurately correlates with Cardiac Output. As discussed in the preamble of the specification, other devices which are capable of monitoring blood flow could be used instead of continuous wave Dopplers.

As discussed above, a pulse oximeter may also be used to provide a monitoring device in accordance with the present invention.

Pulse oximeters are currently designed to measure the transmission of red and infra-red light from haemoglobin of the arterial blood and estimate the arterial oxygen saturation. However, changes in the reflective wavelength of the light from the tissue bed depend on:

A. Changes in the oxy-haemoglobin level.
B. Changes in the total mass of tissue including red blood cells.

Once a pulse oximeter is functioning on a patient, it assumes that the background tissue and blood "mass" is constant (fixed), it focuses on the pulsatile part of perfusions or blood flow wave form and therefore assumes that changes in the wavelength of the light are due to changes in oxygenation.

Typically during anaesthesia, patients breath high inspired concentrations of oxygen. Therefore, changes in light absorption are far more commonly due to changes in the mass of red blood cells (i.e., the assumed to be constant light absorption) than to changes in arterial oxygenation.

To modify a pulse oximeter, we need to work form the principle that using two light wavelengths (one in the visible red spectrum and one in the infra-red spectrum): at the isobestic wavelength, the absorbing power of oxyhaemoglobin in the reduced haemoglobin is the same. Therefore total absorbency depends only on the sum of the two and not the state of oxygenation. Therefore the total absorbency depends only on the total amount of blood present. As tissue blood flow increases or decreases, the total absorbency at the isobestic point will change and this can be used to give a measure of the relative change in blood (mass) flow in the tissue bed. Such a device can therefore be used to monitor changes in blood flow in peripheral tissue beds.

Electromagnetic flow meters have been designed to be surgically implanted around large blood vessels such as the aorta and renal artery. It is possible that such a device may be adapted to be placed around a peripheral tissue bed, such as a finger or tail, to provide an indication of relative changes in blood flow. This may not be accurate, however.

There is no reason that an electromagnetic flow meter could not be used in the present invention, by implantation of a cuff type flow meter around a blood vessel. This is, however an invasive technique, and although it falls within the scope of the present invention it is not preferred.

Other available devices which could be adapted in accordance with the present invention are non-invasive optical flow meters. These devices measure the absorption characteristics of light scattered by blood flowing through tissues such as skin surface, detecting this reflected light, analysing the frequency of the wave forms to obtain the mean peak light frequencies in estimating blood flow. Problems with this approach are that the device only measures very superficial (i.e., skin surface) blood flow, which during anaesthesia is altered by vaso constriction such as caused by changes in body temperature. The device is also subject to movement artefacts/vibration such as caused by patient positioning, movement by surgical manipulations, restorations, vibrations from re-circulating water beds, etc. It is therefore difficult to get a continuous measure from a wave (pre-anaesthesia) through to anaesthesia when positioned for surgery.

Further, the signal requires considerable damping to get a stable measurement, which sacrifices the accuracy of the "real time" measurement. It also relies on estimating the Doppler signal change in the scattered light to obtain the peak frequency and fails to measure perfusion of deeper tissues. Nevertheless, although not preferred, it is quite possible that such a device could be used in the present invention.

Figure 8:
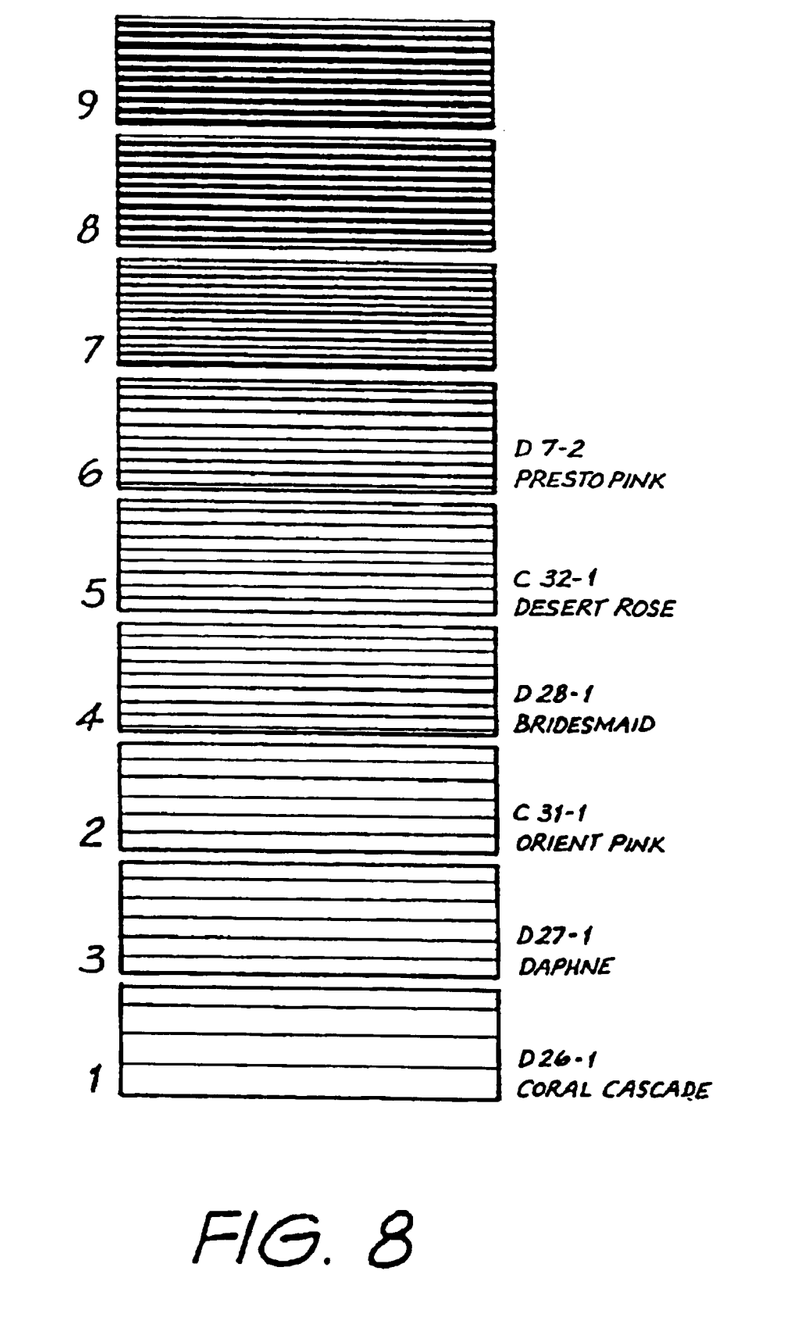
FIG. 8 is a view of a "colour chart" in accordance with an embodiment of the present invention.

The above description is of a relatively sophisticated device which can be used with the method in accordance with the present invention. As discussed in the preamble, a primitive device, in the form of a "colour chart" can also be used. Colours indicating various flow rates would be established by clinical trials for various species in order to produce the colour chart. An anaesthetist will then have reference to the colour chart and compare with the colour of the part of the body concerned such as the oral mucosa, in order to monitor flow rate in the subject. An example colour chart is schematically illustrated in FIG. 8.

It will be appreciated by persons skilled in the art that numerous variations and/or modifications may be made to the invention as shown in the specific embodiments without departing from the spirit and scope of the invention as broadly described. The present embodiments are, therefore, to be considered in all respects as illustrative and not restrictive.

What is claimed is:

1. A method of monitoring a haemodynamic function of one of a human and animal subject to facilitate application of an anaesthetic dose to the subject, the method comprising the step of:
   monitoring blood flow in one of a peripheral blood vessel and a tissue bed;
   generating an indication of changes in the monitored blood flow in one of peripheral blood vessel and as a cardiac output; and
   varying administration of the anaesthetic dose to the subject based upon the cardiac output.

2. The method in accordance with claim 1 further comprising the step of monitoring a relative change in blood flow to provide an indication of a relative change in cardiac output.

3. The method in accordance with claim 1, further comprising the step of carrying out the monitoring blood flow step non-invasively.

4. The method in accordance with claim 1, further comprising the step of carrying out the monitoring blood flow step continuously.

5. The method in accordance with claim 1, further comprising the step of setting a predetermined limit for a blood flow rate, and outputting an alarm which indicates an alarm condition when the blood flow rate reaches the predetermined limit.

6. The method in accordance with claim 1, further comprising the step of pre-setting one of (1) a base reference level for the blood flow rate indicative of a blood flow level of the subject at rest prior to monitoring of the haemodynamic function and (2) an average flow level for a particular type of subject prior to monitoring of haemodynamic function.

7. The method in accordance with claim 6, further comprising the step of processing the signal to produce a display which indicates the trend of the cardiac output.

8. The method in accordance with claim 1, further comprising the step of, during monitoring the blood flow, employing a device which produces a signal which varies with variations in the blood flow rate, and processing the signal to produce an output providing an indication of variations in cardiac output.

9. The method in accordance with claim 8, further comprising the step of modifying the signal by an adjustment factor obtained by a regression analysis of the subject.

10. The method in accordance with claim 8, further comprising the step of modifying the signal by an adjustment factor obtained from a co-variate parameter.

11. The method in accordance with claim 10, further comprising the step of using a heart rate of the subject as the co-variate parameter.

12. The method in accordance with claim 1, further comprising the step of applying a Doppler effect to monitor blood flow.

13. The method in accordance with claim 1, further comprising the step of employing an infrared blood flow sensor to monitor the blood flow.

14. The method in accordance with claim 1, further comprising the step of employing an electromagnetic flow meter to monitor the blood flow.

15. The method in accordance with claim 1, further comprising the step of employing a color chart to monitor the blood flow, and comparing a color of a predetermined part of a body of the subject with the color chart to provide an indication of cardiac output.

16. The method in accordance with claim 1, further comprising the step of monitoring the color of a part of a body of the subject to monitor the blood flow.

17. The method in accordance with claim 1, further comprising the step of monitoring the haemodynamic function of the subject during anaesthesia.

18. The method in accordance with claim 1, further comprising the step of monitoring the haemodynamic function during critical care in a hospital.

19. The method in accordance with claim 1, further comprising the step of monitoring a haemodynamic function during a stress test of the subject.

20. A device for monitoring haemodynamic function in one of a human and animal subject to facilitate application of an anaesthetic dose to the subject, the device comprising;

a blood flow for monitoring changes in blood flow of one of a peripheral vessel and tissue bed, the blood flow monitor including a mechanism to provide an indication of changes in cardiac output; and means for indicating, upon the cardiac output, that a variation of the anaesthetic dose to the subject is required.

21. The device in accordance with claim 20, wherein the blood flow monitor is arranged to monitor a relative change in blood flow of the subject to provide an indication of a relative change in cardiac output.

22. The device in accordance with claim 20, wherein the device further includes processing means for processing a signal from the blood flow monitor to produce an output signal which provides an indication of changes in cardiac output.

23. The device in accordance with claim 22, wherein the processing means is arranged to adjust the signal by an adjustment factor obtained from a regression analysis of the subject.

24. The device in accordance with claim 22, wherein the processing means adjusts the signal by an adjustment factor obtained from a co-variate.

25. The device in accordance with claim 24, wherein the co-variate input is a heart rate of the subject.

26. The device in accordance with claim 22, wherein the device further comprises a display, and the processing means is arranged to control the display to provide an indication of changes in the cardiac output in the subject.

27. The device in accordance with claim 26, wherein the device is arranged to display a base reference value to be compared with a monitored value generated during monitoring of haemodynamic function.

28. The device in accordance with claim 26, wherein the device displays a trend analysis for changes in cardiac output which shows the trend of the changes in cardiac output.

29. The device in accordance with claim 20, wherein the blood flow monitor comprises a Doppler sensor adapted to monitor blood flow changes.

30. The device in accordance with claim 20, wherein the blood flow monitor comprises an infrared sensor for monitoring blood flow.

31. The device in accordance with claim 20, wherein the blood flow monitor comprises an electromagnetic flow meter.

32. The device in accordance with claim 20, wherein the blood flow monitor includes a color chart can be compared with a color of a predetermined part of a body of the subject.

* * * * *